United States Patent [19]

Rorstad et al.

[11] Patent Number: 5,401,727
[45] Date of Patent: Mar. 28, 1995

[54] PROCESS FOR ENHANCING THE RESISTANCE OF AQUATIC ANIMALS TO DISEASE

[75] Inventors: Gunnar Rorstad; Borre Robertson; Jan Raa, all of Bartlesville, Okla.

[73] Assignee: AS Biotech-Mackzymal, Tromso, Norway

[21] Appl. No.: 190,435

[22] Filed: Feb. 2, 1994

Related U.S. Application Data

[62] Division of Ser. No. 549,575, Jul. 6, 1990.

[51] Int. Cl.⁶ .................. A61K 31/715; A01N 43/16; C07H 1/08; C08B 37/00
[52] U.S. Cl. ...................... 514/54; 514/885; 536/123.12; 536/124
[58] Field of Search ................. 514/54, 885; 536/123.12, 124

[56] References Cited

U.S. PATENT DOCUMENTS 4,739,046  4/1988  Di Luzio .................. 536/117

*Primary Examiner*—Douglas W. Robinson
*Assistant Examiner*—Francisco C. Prats
*Attorney, Agent, or Firm*—Richmond, Phillips, Hitchcock & Fish

[57] ABSTRACT

The present invention provides a process for stimulating the immune system of aquatic animals of the class Osteichthyes and subphylum Crustacea comprising administering an effective amount of a yeast cell wall glucan composed of glucopyranose units linked by predominately beta-1,3 glycosidic bonds, having at least one branch therefrom of glucopyranose units linked by beta-1,6 glycosidic bonds. Additionally the invention provides a process for enhancing the effect of vaccines by administering an effective amount of the described yeast cell wall glucan along with vaccine antigens. Further this invention also provides a process for obtaining a glucan particularly effective for stimulating the immune system of aquatic animals of the class Osteichthyes and subphylum Crustacea.

2 Claims, 5 Drawing Sheets

PROCESS FOR ENHANCING THE RESISTANCE OF AQUATIC ANIMALS TO DISEASE

This application is a divisional of application Ser. No. 07/549,575, filed Jul. 6, 1990.

FIELD OF THE INVENTION

This invention relates to the use of glucans as a prophylactic medicament for aquatic animals.

BACKGROUND OF THE INVENTION

Vaccines and antibiotics are currently the only two proven means for protecting aquatic animals of the classes Osteichtyes and Crustacea from disease in aquacultural settings. However, several of the pathogenic diseases caused by bacterial, vital, fungal and protozoan diseases, cannot be effectively prevented by vaccination nor treated with antibiotics. Several workers in the field have tried to develop alternative prophylatic treatments for aquatic animals in the classifications Osteichthyes and Crustacea in aquacultural settings, particularly the use of immunostimulatory compounds.

Although little is known about the immune system of fish and crustaceans, some compounds do appear to enhance the microbe killing activity of macrophages in fish. It has been reported that killed mycobacteria and muramyl peptides have enhanced the resistance of rainbow trout (*Salmo gairdneri* Richardson) against several pathogens. Additionally, it appears that extracts from a marine tunicate will increase the resistance of American eels (*Anguilla rostrata* LeSeur) against infection by *Aeromonas hydraphila*. However, none of these compounds have been demonstrated to be a suitable means for protecting fish or crustaceans from diseases in aquacultural settings.

Immunostimulatory compounds have also been identified which are effective for mammalian systems such as glucan. Glucan generically refers to a variety of polysaccharides containing glucose as the only glycosyl unit. Previous studies have demonstrated that specific beta-1,3 glucans are potent activators of macrophage/monocyte cell series and complement as well as lymphocytes of experimental warm-blooded animals. Some evidence has even suggested that glucan may activate arthropod and plant host defense mechanisms. Additionally no studies have yet been published which establish that yeast glucans actually function as immunostimulator in aquatic animals in the classifications Osteichthyes (such as salmon and trout) and Crustacea (such as lobsters and shrimp) in aquacultural settings.

Therefore, it would be a significant contribution to the aquacultural industry to provide a means of enhancing the resistance of aquatic animals In of the classifications Osteichthyes and Crustacea to disease.

It is thus an object of the present invention to provide a glucan preparation from yeast which enhances the resistance of aquatic animals in the classifications Osteichthyes and Crustacea to diseases in aquacultural settings.

Additionally, it is an object of the present invention to provide a process for the production of a glucan preparation suitable for administration to aquatic animals in the classifications Osteichthyes and Crustacea in aquacultural settings.

Further it is an object of the present invention to provide a process for enhancing the resistance of aquatic animals in the classifications Osteichthyes and Crustacea in aquacultural settings to diseases by administering an effective amount of a glucan preparation.

It is also an object of the present invention to provide a process for enhancing the effect of vaccines for aquatic animals in the classifications Osteichthyes and Crustacea in aquacultural settings by administering an effective amount of a glucan preparation together with the vaccine antigen(s).

SUMMARY OF THE INVENTION

In accordance with the present invention we have discovered a process for stimulating the immune system of an aquatic animal selected from the group consisting of the class Osteichthyes and subphylum Crustacea in aquacultural settings comprising:

Administering a yeast glucan composed of glucopyranose units linked predominately by beta-1,3 glycosidic bonds, having at least one branch therefrom of glucopyranose units linked by beta-1,6 glycosidic bonds to stimulate the immune system of the aquatic animal.

In accordance with the present invention we have also discovered a process for enhancing the effect of a vaccine administered to an aquatic animal selected from the group consisting of the class Osteichthyes and subphylum Crustacea in aquacultural settings comprising:

administering a yeast glucan prior to or in combination with a vaccine to enhance the production in the aquatic animal of specific antibodies against the vaccine antigens.

In accordance with another aspect of the present invention we have also discovered a process for the production of a yeast glucan composed of glucopyranose units linked predominately by beta-1,3 glycosidic bonds having at least one branch therefrom of glucopyranose units linked by beta-1,6 glycosidic bonds comprising:

(a) alkali-extracting suitable glucan-containing yeast cells with a suitable extractive aqueous alkali solution under suitable conditions to provide a first insoluble yeast residue;

(b) hot alkali-extracting said first insoluble yeast residue with a suitable extractive aqueous alkali solution under suitable extraction conditions wherein the hot alkali extraction is performed at least 2 times to provide a second insoluble yeast residue and recovering the insoluble yeast residue after each hot alkali extraction; thereafter (c) washing said second insoluble yeast residue under suitable conditions with water at a pH in the range of from about pH 4 to about pH 7 thereby providing a third insoluble yeast residue and recovering said third insoluble yeast residue after the wash;

(d) hydrolyzing said third insoluble yeast residue with a suitable hydrolyzing acid under suitable hydrolysis condition wherein the acid hydrolysis is performed at least 3 times to provide a fourth insoluble yeast residue and recovering the insoluble yeast residue after each acid hydrolysis; thereafter (e) boiling said fourth insoluble yeast residue under suitable conditions in water wherein the boiling of said fourth insoluble yeast residue is performed at least 2 times to provide a fifth insoluble yeast residue and recovering the insoluble yeast residue after each boiling; and (f) boiling said fifth insoluble yeast residue under suitable conditions in ethanol wherein the boiling in ethanol of said fifth yeast residue is performed at least 2 times to provide a sixth insoluble yeast residue and recovering the insoluble yeast residue after each boiling; thereafter (g) washing said sixth Insoluble yeast residue under suitable conditions with water wherein the washing of said washed sixth insoluble yeast residue is performed at least 2 times to provide a yeast glucan and recovering the insoluble yeast residue after each wash.

DETAILED DESCRIPTION OF THE INVENTION

Figure 1:
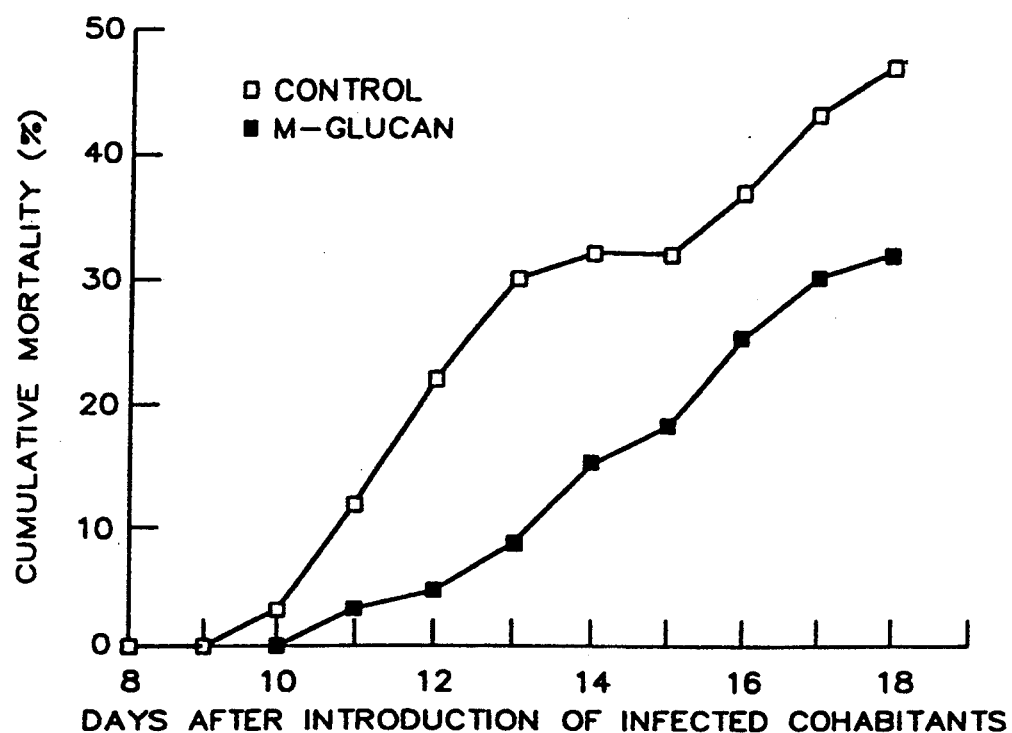
FIG. 1 provides the cumulative mortality in Atlantic salmon fed with M-glucan or a control diet after being challenged with furunculosis (*Aeromonas salmonicida* subspecies salmonicida).

We have discovered that a particular class of yeast glucans is very effective as a prophylactic medicament for aquatic animals in the classifications Osteichthyes and Crustacea.

Osteichthyes is a commercially important class of fish which includes but is not limited to fish selected from the group consisting of salmons, trouts, whitefishes, catfishes, milkfishes, carps, cichlids (such as tilapia), dolphins (also known as mahi-mahi), sturgeons, paddlefishes, perches (such as walleye, sauger and yellow perch), jacks and pompanos (such as yellowtails), sea basses (such as groupers), stripped basses, porgies (such as sea breames), codfishes, flatfish (such as flounder, halibut, turbot and dab), sunfishes, herrings, anchovies, smelts, pikes, snappers (such as red drum or redfish), drums, mullets, rabbitfishes, mackerels, tunas, puffer fishes and eels (such as American, European and Asiatic eels). These fishes are generally fish from the families selected from the group consisting of Salmonidae (including the subfamily Coregonidae), Ictaluridae, Chanidae, Cyprinidae, Cichlidae, Coryphaenidae, Acipenseridae, Polyodontidae, Percidae, Serranidae, Percichthyidae, Carangidae, Sparidae, Gadidae, Bothidae, Pleuronectidae, Soleidae, Clupeidae, Engraulidae, Osmeridae, Esocidae, Lutjanidae, Sciaenidae, Mugilidae, Siganidae, Scombridae, Centrarchidae, Tetraodontidae, Anguillidae, Muraenidae, and Congridae. This prophylactic medicament is believed to be particularly valuable for protecting members of the family Salmonidae selected from the group consisting of *Salmo salar, Salmo clarkii, Salmo gairdenri, Salmo trutta, Oncorhyncus keta, Oncorhynchus gorbuscha, Oncorhynchus tshawytscha, Oncorhynchus kisutch, Oncorhynchus nerka, Salvelinus alpinus, Salvelinus fontinalis, Salvelinus malma* and *Salvelinus namaycush*. Additional this prophylactic medicament is also believed to be suitable for protecting aquarium fishes and/or ornamental fishes which are suitable for maintaining in salt water or fresh water aquariums by hobbist.

Crustacea is a commercially important subphylum of shellfish which Includes but is not limited to shellfish selected from the group consisting of shrimp, prawns (such as macrobrachum prawns), lobsters (such as spiny and spanish or slipper lobsters), crayfish and crabs (such as crabs selected from the group consisting of king crab, stone crab, rock crab, dungeness crab, snow crab, and blue crab). This prophylactic medicament is believed to be particularly valuable for protecting members of the family Penaeidae selected from the group consisting of *Penaeus monodon, Penaeus chinensis, Penaeus indicus, Penaeus stylirostris, Penaeus merguiensis, Penaeus vannamei, Metapeneus ensis, Penaeus setiferus, Penaeus japonis, Penaeus aztecus, Penaeus duorarum, Penaeus semisulcatus, Penaeus teraoi, Penaeus orientalis, Penaeus plebejus,* and *Penaeus kerathurus.*

Additionally this prophylatic medicament is believed to be effective for lobsters such as lobster from the families Homaridae and Palinuridae selected from the group consisting of *Homarus americanus, Homarus gammarus, Palinarus elephas, Palinarus interruptus, Palinarus argus* and *Nephrops norvegicus.*

Glucan generally refers to a variety of polyglucans. Glucan, however, as described herein will refer to polyglucoses obtained from yeast cell walls and which are branched and unbranched chains of glucopyranose molecules (or units) linked together by predominately beta-1,3 and beta-1,6 glycosidic bonds. From our experiments with yeast glucans it appears that glucans having a chain of glucopyranose units linked by beta-1,3 bonds with at least one branch of glucopyranose units linked by beta-1,6 bonds is the most effective prophylactic medicament for aquatic animals in the classificatons Osteichthyes and Crustacea. The preferred glucan should be a chain of from about 400 to about 1500 glucopyranos units having predominately beta-1,3 glycosidic bonds with at least on branch linked thereto of glucopyranose units linked predominately by beta-1,6 glycosidic bonds. Each of the branches composed of glucopyranose units linked predominately by beta-1,6 glycosidic bonds should preferably have from in the range of 1 to about 10 glucopyranose units and most preferably each branch will have in the range of from 1 to 6 glucopyranose units.

The preferred glucan for the practice of the present invention is a yeast glucan preparation which we have designated as M-glucan. M-glucan is a highly branched glucan composed of a chain of glucopyranose units linked by beta-1,3 glycosidic bonds with branches linked thereto of from about 1 to about 6 glucopyranose units linked by beta-1,6 glycosidic bonds. This glucan is further characterized by being insoluble in dilute alkali and acid solution as well as being insoluble in ethanol.

Suitable glucans can be prepared from a variety of microbial sources. A non-exhaustive list of such sources is presented in Table I.

Table I

Examples of Sources of Glucans which can be employed:

*Candida utilis*
*Candida tropicalis*
*Geotrichum candidum*
*Hansenula anomala*
*Hansenula polymorpha*
*Kloeckera brevis*
*Kloeckera apiculata*
*Kluyveromyces bulgaricus*
*Kluyveromyces fragilis*
*Phaffia rhodozyma*
*Pichia fermentans*
*Pichia pastoris*
*Saccharomyces cerevisiae*
*Saccharomyces carlsbergensis*

The preferred microbial sources of suitable glucans for the practice of the present invention is *Saccharomyces cerevisiae, Candida utilis* and *Pichia pastoris.*

The glucan used in the practice of the present invention can be prepared from microbial sources utilizing suitable extraction means known to those skilled in the art. One method for extracting glucans from the cell walls of *Saccharomyces cerevisiae* utilizes successive extraction with hot alkali and acetic acid followed by aqueous washes to remove soluble components in the cell walls. The residual insoluble material is the glucan product of interest.

To extract the preferred M-glucan, the following extraction process should be used. First the yeast should be alkali extracted at least once by suspending the yeast in an aqueous alkali solution of from about 50 gram of dry yeast/liter of aqueous alkali solution to about 300 gram of dry yeast/liter of aqueous alkali solution. The extractive aqueous alkaline solution should have an alkali concentration from about 2 weight percent/liter to about 6 weight percent/liter. The alkali compound utilized in the extractive alkali solution may be selected from the group consisting of NaOH, KOH, Ca(OH)$_2$ and Na$_2$CO$_3$. The suspension containing the yeast in and the aqueous alkali solution should be stored at a temperature in the range from about 20° C. to about 30° C. for from about 16 hours to about 30 hours. The insoluble yeast residue provided by the alkali extraction may be recovered iron the supernatant by any suitable separatory means known to those skilled in the art, including but not limited to filtration, crossflow filtration or centrifugation. The insoluble yeast residue collected by the separating means should next be extracted with a hot aqueous alkali mixture.

The insoluble yeast residue may next be suspended in a second extractive aqueous alkali solution corresponding to about 50 gram of dry yeast/liter of extractive aqueous alkali solution to about 300 gram of dry yeast/liter of extractive aqueous alkali solution. The concentration of the above specified alkali compound should range from about 1 weight percent/liter to about 4 weight percent/liter. The temperature at which the insoluble yeast residue is suspended in the extractive aqueous alkali solution should be in the range of from about 60° C. to about 100° C. in the range of about 1 hour to about 6 hours. The suspension should then be allowed to cool to room temperature, preferably by maintaining the suspension at room temperature overnight.

The insoluble yeast residue from the hot aqueous alkali extraction is next separated from the supernatant by any suitable separatory means known to those skilled in the art including, but not limited to filtration, crossflow filtration or centrifugation. After the insoluble yeast residue is collected, the hot extraction with the aqueous alkali solution should be performed at least twice and preferably from in the range of about 2 to about 5 times with the insoluble yeast residue being collected at the end of each extraction.

Following the extraction of the insoluble yeast residue with the hot aqueous alkali solution, the pH of the insoluble yeast residue should be brought into the range of from about 4 pH to about 7 pH, with a suitable aqueous acid (suitable examples of which include inorganic acid, such as hydrochloric acid, phosphoric acid, sulphuric acid or organic acid such as formic acid, acetic acid, propionic acid, oxalic acid and other like acids), and washed with water. The washes would be performed by suspending the insoluble yeast residue in water followed by stirring and then separation of the insoluble yeast residue from the water by any suitable separation means such as filtration, crossflow filtration or centrifugation.

Following the alkali extraction and washes the insoluble yeast residue should next be subjected to mild acid hydrolysis. The insoluble yeast residue should be contacted with an aqueous acid selected from the group consisting of acetic acid, trifluoroacetic acid, hydrochloric acid, phosphoric acid, and sulfuric acid. The hydrolyzing acid should be provided in an aqueous concentration of from about 0.05 moles/liter to about 1 mole/liter. The insoluble yeast reside should be mixed in the range of from about 10 grams (dry weight) of insoluble yeast residue/liter of aqueous hydrolyzing acid to about 50 grams (dry weight) of insoluble yeast residue/liter of aqueous hydrolyzing acid. The mixture of insoluble yeast residue and aqueous hydrolyzing acid solution should be maintained at a temperature of from about 60° C. to about 90° C. for in the range of about 3 hours to about 6 hours. The insoluble yeast residue is then separated from the aqueous hydrolyzing acid solution by any suitable separating means known to those skilled in the art including but not limited to filtration, crossflow filtration or centrifugation under suitable conditions. After the insoluble yeast residue is collected from the mixture, the acid hydrolysis should be performed at least three times and preferably from in the range of about 3 to about 10 times with the resulting insoluble yeast residue being collected at the end of each extraction.

After the final extraction the resulting insoluble yeast residue should then be dispersed in a concentration of from about 10 grams (dry weight) of insoluble yeast residue/liter of water to about 50 grams (dry weight) of insoluble yeast residue/liter of water, and boiled for about 0.5 hours to about 2 hours. This procedure should be performed at least twice and preferably from in the range of about 2 to about 6 times. Between each treatment in boiling water the insoluble yeast residue may be recovered from the liquid phase by any suitable separatory means such as filtration, crossflow filtration or centrifugation.

The insoluble yeast residue should also be dispersed in from about 20 grams (dry weight) insoluble yeast residue/liter of ethanol to about 100 grams (dry weight) insoluble yeast residue/liter of ethanol and boiled from about 0.1 hours to about 2 hours. The insoluble yeast residue may be recovered after cooling by any suitable separatory means such as filtration, crossflow filtration or centrifugation. The boiling in ethanol should be performed at least twice and preferably from in the range of about 2 to about 6 times.

Finally the insoluble yeast residue should be washed at least twice and preferably from in the range of from about 2 to about 6 times with water at room temperature. After each wash with water the insoluble yeast residue may be recovered by any suitable separatory means including filtration, crossflow filtration or centrifugation.

Suitable glucans can be prepared also from the by-product of yeast extract manufactured by subjecting the isoluble residue after extracting the yeast to further alkali extraction and acid treatment as described herein.

Routes and Methods of Administration

The glucans of the present invention can be administrated by a number of routes, including but not limited to: enteral (oral), via aqueous exposure, and parenteral (injection including but not limited to intradermally, intraperitoneally, subcutaneously, and intramuscularly). When administered to aquatic animals of the class Osteichthyes or subphylum Crustacea, the glucan can be employed in admixture with conventional excipient, i.e., suitable pharmaceutically acceptable organic and inorganic carrier substances which do not deleteriously react with the glucan. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, and the like. The pharmaceutical preparations can be sterilized and, if desired, mixed with auxiliary agents, e.g., lubricants, preservatives, stablizers, wetting agents, emulsifiers, salts for influencing osmotic pressure, buffers and the like which do not deleteriously react with the glucan. They can also be combined where desired with other active agents, e.g., vitamins. For parenteral application, particularly suitable are injectable, sterile solutions, preferably oily or aqueous solutions as well as suspensions or emulsions. For enteral (oral) the glucans of the present invention can also be administered orally in a dry or moist form or optionally provided admixed with aquatic feeds. Additionally, glucan may be administered concurrently with at least one suitable antimicrobial agent and/or at least one suitable vaccine, When a glucan and an antimicrobial agent and/or vaccine is administered, each agent may be successively administered, or glucan may be combined with one or more antimicrobial agents or vaccines and administered as a single composition.

The amount of glucan provided per kilogram aquatic animal weight should be an amount sufficient to provide an immunostimulatory effect to the aquatic animal to which it is provided. The effective amount of injected glucan per kilogram of aquatic animal body weight should be in the range of from about 5 milligrams of glucan/kilogram of biomass to about 100 milligrams of glucan/kilogram of biomass. If the glucan is provided orally in dry form the amount of glucan per kilogram of body weight should be in the range of from about 5 mill/grams of glucan/kilogram of biomass to about 100 milligrams of glucan/kilograms of biomass when provided on a daily basis. In dry form such as in dry diets for aquatic animals the amount of glucan in the diet may range from 1 gram of glucan/kilogram diet to about 10 grams of glucan/kilogram diet. Diets suitable for aquatic animals of the class Osteichthyes and subphylum Crustacea are well known in the art.

It will be appreciated that the actual preferred amounts of glucan in a specific case will vary according to the particular compositions formulated, the mode of application, and the particular situs and organism being treated. Dosage for a given host can be determined using conventional considerations, e.g., by customary comparison of the differential activities of the glucan and of a known agent, e.g.,by means of an appropriate, conventional pharmacological protocol. After administration of the glucan a delay may occur before the immunostimulatory effect is first observable. Thus, disease resistance may not immediately be enhanced, however, it is believed that within 14 days of administration an immunostimulatory effect will be observed. When the glucan has been administered by oral feeding a certain delay will also be observed, however, after approximately 21 days of feeding the glucan the enhanced disease resistance should manifest itself. As long as the glucan is provided in feed on a daily or semi-daily basis enhanced disease resistance should continue. Even after feeding of the glucan is discontinued that enhanced resistance to disease should continue, the duration depending on the dosage/kilogram of biomass and the duration of feeding of glucan.

The following series of Examples are presented for purposes of illustration and not by way of limitation on the scope of the invention.

EXAMPLE I

This example provides the protocol used to obtain an immunostimulatory glucan suitable for utilization in the practice of the present invention.

500 grams of dry *Saccharomyces cerevisiae* was suspended in 3 liters of 6 percent by weight aqueous NaOH solution. This suspension was then stirred overnight at room temperature. After stirring the suspension was centrifuged at 2000× g for 25 minutes. The supernatant was discarded and the insoluble residue was then resuspended in 3 liters of 3 percent NaOH and incubated for three hours at 75° C. followed by cooling the suspension overnight. The suspension was then centrifuged at 2000× g for 25 minutes and the supernatant was decanted. The residue was then resuspended In 3 percent NaOH, heated and centrifuged as previously described.

The insoluble residue remaining was then adjusted to pH 4.5 with acetic acid. The insoluble residue was then washed successively with 2 liters of water three times and recovered by centrifuging at 2000× g for 25 minutes after each wash (the supernatant was poured off). The residue was then suspended in 3 liters of a 0.5M aqueous acetic acid. The suspension was heated for 3 hours at 90° C. The suspension was then cooled to room temperature. After cooling, the insoluble residue was collected by centrifuging at 2000× g for 25 minutes. This treatment (from adjusting to pH 4.5 to collecting the cooled residue) was repeated 7 times.

The insoluble residue was then suspended in 3 liters of distilled water and stirred for 30 minutes at 100° C., then cooled and centrifuged at 2000× g for 25 minutes. The supernatant was discarded. The insoluble residue was washed in this manner 4 times. The residue was next suspended in 2 liters of ethanol and heated at 78° C. for 2 hours. This wash with ethanol was repeated 4 times. The residue was then washed 4 times with 3 liters of distilled water at room temperature to remove any trace of the ethanol.

EXAMPLE II

This example demonstrates the effectiveness of M-glucan as a prophylactic medicament in enhancing the fish of the class Osteichthyes specifically Atlantic salmon's (*Salmo salar*) resistance to furunculosis (*Aeromonas salmonicida* subspecies salmonicida).

Pre-smolt Atlantic salmon with an average weight of 30 grams per fish were obtained from a local smolt producer and kept in 200 liter flow-through tanks supplied with aerated fresh water (maintained at approximately 12° C.). A first group of 60 salmon were fed dry feed at a rate of 1% of fish weight per day. The salmon feed contained 1 g M-glucan per kg dry matter. The salmon were fed for 12 weeks on this diet before being exposed to furunculosis. Similarly a control group of 60 other salmon was fed the salmon feed without M-glucan for 12 weeks. At the end of the 12 week period the two groups of salmon were pooled together in the same tank, and exposed to furunculosis by introducing a number of salmon infected by intraperitoneal injection of 0.1 ml saline containing $1 \times 10^3$ *Aeromonas salmonicida* subspecies salmonicida per fish. The number of cohabiting infected fish introduced corresponded to 10% (12 fish) of the total number of fish in the tank. After the groups of salmon had been combined the diet consisted of the control feed.

FIG. 1 presents the mortality percentage throughout the test period. The final mortality percentage of the salmon fed M-glucan was approximately 33% less than the control salmon. The reduced mortality percentages for the salmon fed M-glucan demonstrates that M-glucan is effective as prophylactic medicament for fish of the class Osteichthyes against furunculosis (*Aeromonas salmonicida* subspecies salmonicida). This example also demonstrates that M-glucan may be effectively utilized in an aquatic feed as a prophylactic medicament against disease.

EXAMPLE III

This example demonstrates the effectiveness of M-glucan as a prophylactic medicament in enhancing fish of the class Osteichthyes, specifically Atlantic salmon's (*Salmo salar*) resistance to cold water vibriosis (*Vibrio salmonicida*).

Atlantic salmon with an average weight of 30 gram per fish were obtained from a local smolt producer. The salmon were kept in 200 liter flow-through tanks supplied with aerated fresh water (maintained at approximately 9°-10° C.). At 70 days the water was changed to aerated sea water with ambient temperatures (approximately 9°-10° C.). The seawater was collected by pumping from a nearby commercial salmon farm, which at the time had outbreaks of cold water vibriosis. A first triplicate of randomized groups of 50 salmon were fed a commercial dry pellet at a rate of 1% of body weight per day. The dry feed contained 1 g M-glucan per kg of feed. Similarly, a second triplicate of ranomized control groups of 50 salmon were fed the same salmon feed without M-glucan.

Figure 2:
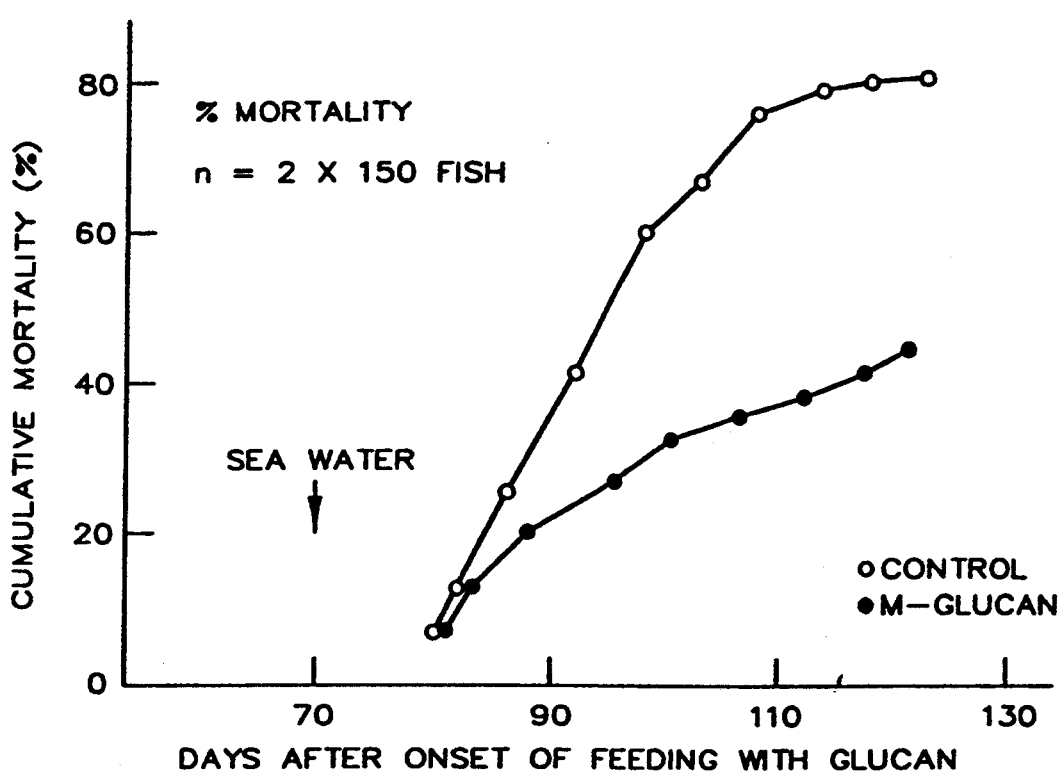
FIG. 2 provides the cumulative mortality in Atlantic salmon fed with M-glucan or a control diet after being challenged with cold water vibriosis (*Vibrio salmonicida*).

FIG. 2 presents the pooled mortality percentages of both feeding regimes caused by a natural infection of cold water vibriosis introduced by the sea water at day 70 from onset of the experiment. The salmon provided with M-glucan in their diet had a significantly reduced mortality percentage compared to the control salmon without M-glucan. This example demonstrates that M-glucan enhances the resistance of fish of the class Osteichthyes to cold water vibriosis (*Vibrio salmonicida*). This example also demonstrates that M-glucan may be effectively utilized in an aquatic feed as a prophylactic medicament against disease.

EXAMPLE IV

This example demonstrates the effectiveness of M-glucan as a prophylactic medicament in enhancing fish of the class Osteichthyes specifically Atlantic salmon's (*Salmo salar*) resistance to classical vibriosis (*Vibrio anguillarum* serotype 01).

Atlantic salmon with an average weight of 30 grams per fish were obtained from a local smolt producer. The salmon were kept in flow-through tanks holding 200 liters of fresh aerated water (maintained at approximately 12° C.). A first group of 40 salmon were fed for 5 weeks at a rate of 1% of body weight per day with a dry feed containing 1 g M-glucan per kg of feed. A control group of 40 salmon were fed for 5 weeks at the same rate with a control diet without M-glucan. By the end of the 5 weeks, the two groups were pooled together in one tank and bath challenged for 45 minutes in seawater with $1 \times 10^6$ *Vibrio anguillarum* 01 per ml. After the challenge, the water was gradually switched back to freshwater and the fish fed the control diet.

Figure 3:
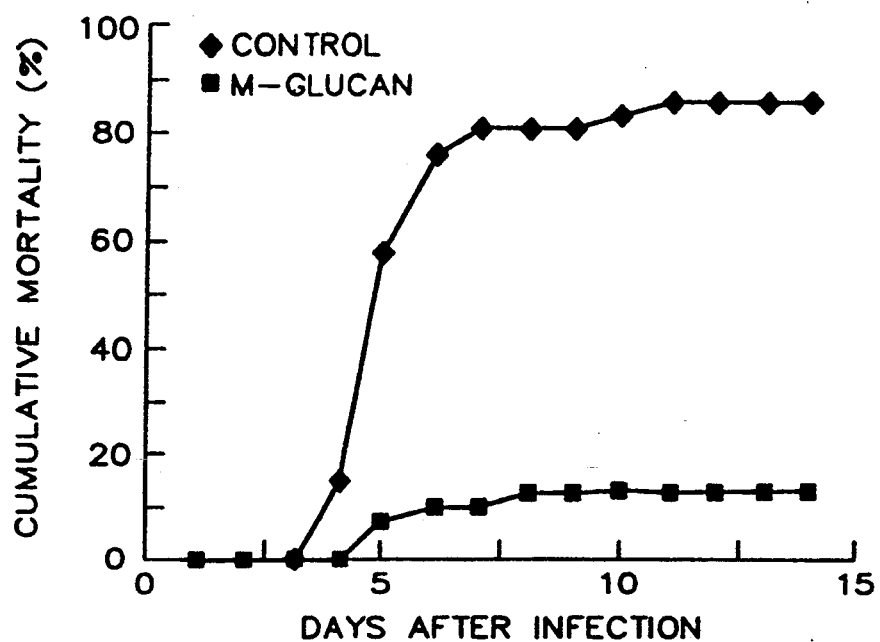
FIG. 3 provides the cumulative mortality in Atlantic salmon fed with M-glucan or a control diet after being challenged with classical vibriosis (*Vibrio anguillarum* serotype 01).

FIG. 3 presents the mortality percentage throughout the test period. The final mortality percentage of the salmon fed M-glucan was approximately 15%, while the mortality in the control group was approximately 85%. The reduced mortality percentages for the salmon fed M-glucan demonstrates that M-gluten is effective as prophylactic medicament for fish of the class Osteichthyes against vibriosis (*Vibrio anguillarum* serotype 01). This example also demonstrates that M-glucan may be effectively utilized in an aquatic feed as a prophylactic medicament against disease.

EXAMPLE V

This example demonstrates the effectiveness of M-glucan as a prophylactic medicament in enhancing fish of the class Osteichthyes specifically Atlantic salmon's (*Salmo salar*) resistance to vibriosis (*Vibrio anguillarum* serotype 01).

Atlantic salmon with an average weight of 20 grams per fish were obtained from a local smolt producer. The salmon were kept in flow-through tanks holding 200 liters of fresh aerated water (maintained at approximately 12° C.). A first group of 40 salmon were injected intraperitoneally with a 0.2 ml suspension containing 2 mg M-glucan in an isotonic saline solution, A control group of 40 salmon were injected intraperitoneally with a 0.2 ml isotonic saline solution. Both groups of salmon were maintained on a commercial dry pellet throughout the experimental period.

Figure 4:
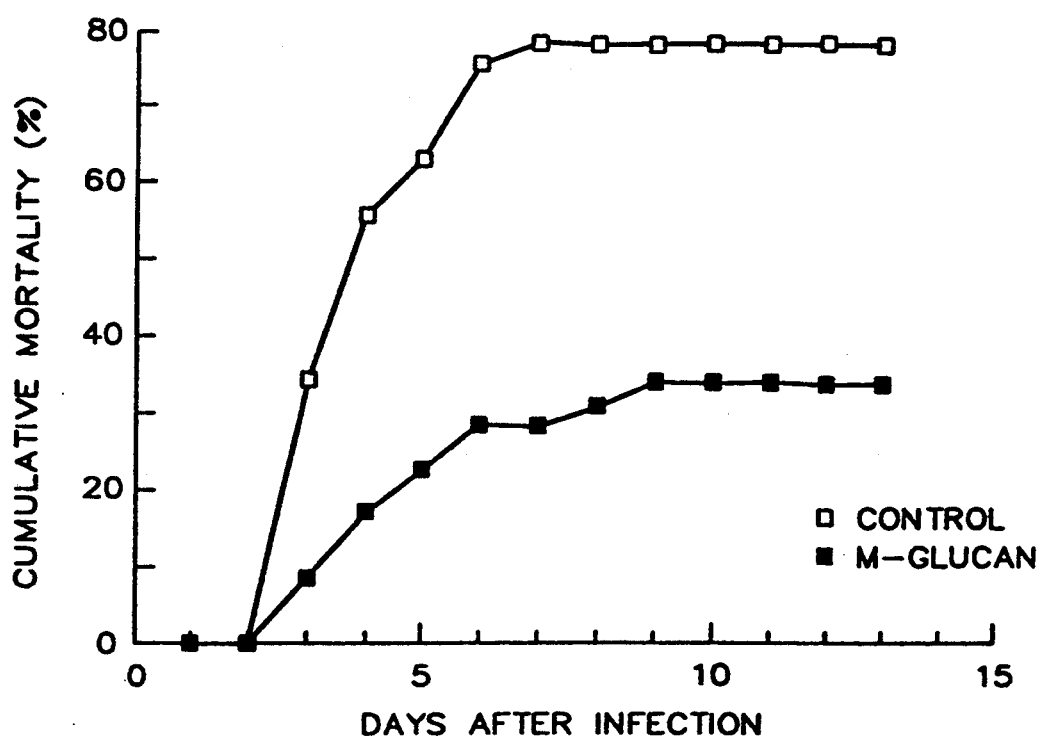
FIG. 4 provides the cumulative mortality in Atlantic salmon treated with M-glucan or a saline solution control after being challenged with classical vibriosis (*Vibrio anguillarum* serotype 01).

Three weeks after the injections both groups of salmon were challenged by injecting intraperitoneally $5 \times 10^4$ live *Vibrio anguillarum* serotype 01 bacterial cells per salmon. FIG. 4 presents a comparison of the mortality percentages of the control group and the first group (which received the M-glucan). As can be seen from FIG. 4 there is a significant reduction (approximately 45%) in mortality percentages for the first group which received M-glucan by intraperitoneal injection. The reduced mortality percentages for the salmon treated with M-glucan demonstrates that M-glucan is an effective prophylactic medicament against classical vibriosis. These data also demonstrates that M-glucan can be effectively administered by injection.

EXAMPLE VI

This example demonstrates the effectiveness of M-glucan as a prophylactic medicament in enhancing fish of the class Osteichthyes specifically Atlantic salmon's (*Salmo salar*) resistance to enteric red mouth disease (*Yersinia ruckeri*).

Pre-smolt Atlantic salmon with an average weight of 20 grams per fish were obtained from a local smolt producer and kept in a 200 liter flow-through tank supplied with aerated fresh water (maintained at approximately 12° C.). A first group of 50 salmon was injected intraperitoneally with a 0.2 ml suspension containing 2 mg of M-glucan in an isotonic saline solution. A control group of salmon was injected with 0.2 ml of a solution containing only isotonic saline. Both groups of salmon were fed a commercial dry pellet throughout the experimental period. After 3 weeks both groups of salmon were challenged by an intraperitoneal injection of $10^4$ live *Yersinia ruckeri* bacterial cells per salmon.

Figure 5:
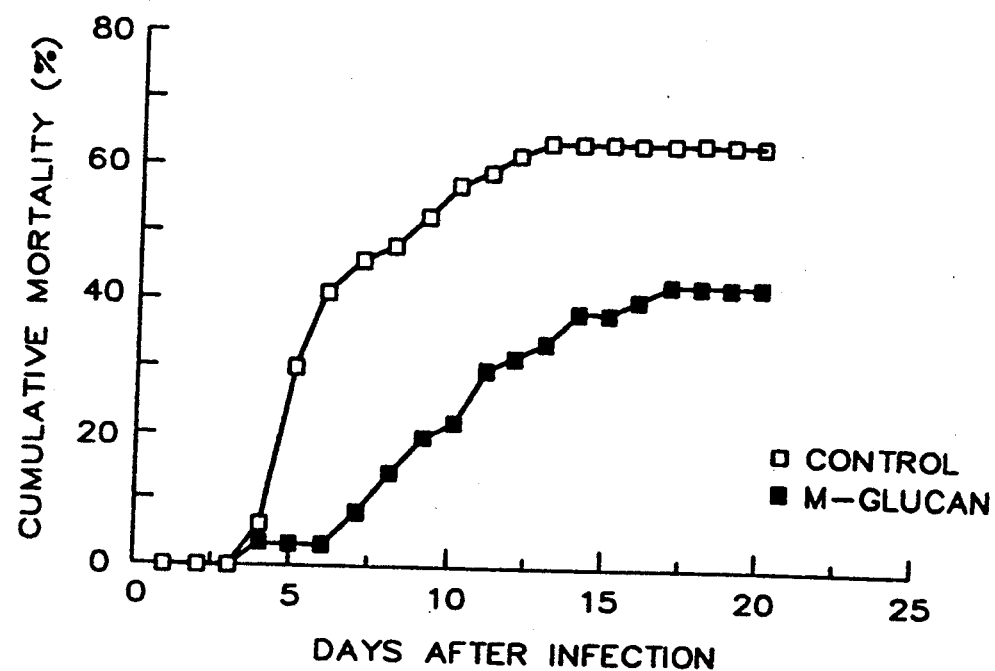
FIG. 5 provides the cumulative mortality in Atlantic salmon treated with M-glucan or a saline solution control after being challenged with red mouth disease (*Yersinia ruckeri*).

FIG. 5 presents the mortality percentages for both groups of salmon. As can be seen from the cumulative mortality percentages the group which received M-glucan had approximately 20% lower mortality compared to the control group which received only an isotonic saline solution. These results demonstrate that M-glucan is an effective prophylactic against enteric red mouth disease. This data also demonstrates that M-glucan can be effectively administered by injection.

EXAMPLE VII

This example compares the effectiveness of M-glucan and D,L-glucan as prophylactic medicaments in enhancing fish of the class Osteichthyes, specifically Atlantic salmon's (*Salmo salar*) resistance to cold water vibriosis (*Vibrio salmonicida*).

Pre-smolt Atlantic salmon with an average weight of 20 gram per fish were obtained from a local smolt producer and kept in a 200 liter flow-through tank suppled with aerated fresh water (maintained at approximately 9°–10° C.). A first group of 50 salmon were injected intraperitoneally with 0.2 ml suspension containing 2 mg M-glucan in an isotonic saline solution.

A second group of 50 salmon were injected intraperitoneally with a 0.2 ml suspension containing 2 mg of D,L-glucan in an isotonic saline solution. The D,L-glucan was prepared from *Saccharomyces cerevisiae* cells following the procedure described by DiLuzio (1979) in *Int. J. Cancer* 24: 773–779. A control group of salmon was injected with 0,2 ml isotonic soline solution. All three groups were maintained on a commercial dry pellet throughout the experimental period. After 3 weeks all three groups of salmon were challenged by an intraperitoneal injection of $5 \times 10^5$ live *Vibrio salmonicida* bacterial cells per fish.

Figure 6:
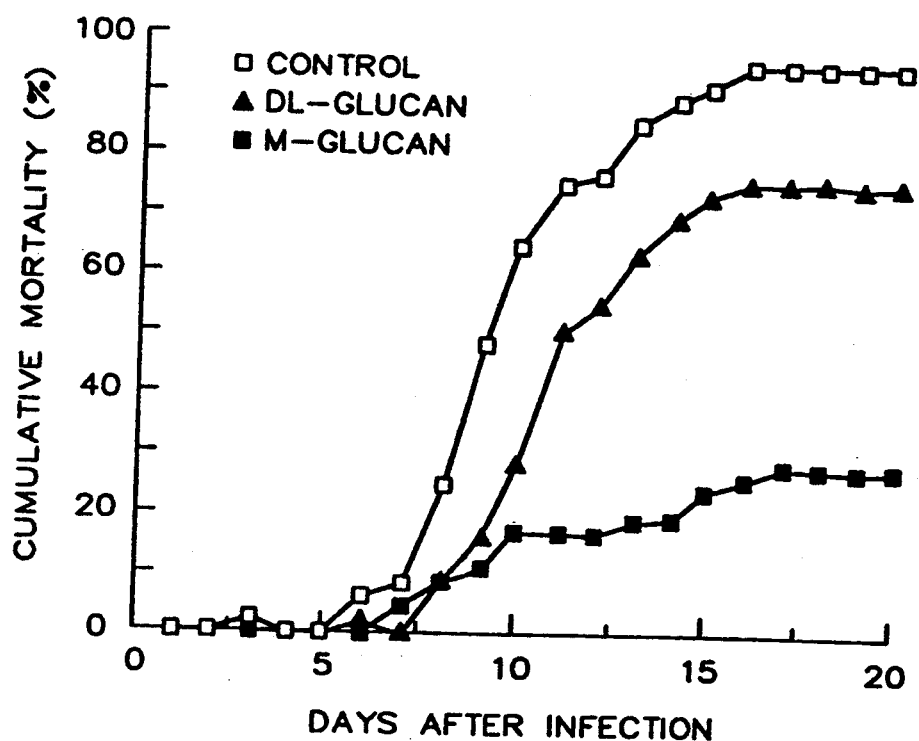
FIG. 6 provides the cumulative mortality in Atlantic salmon treated with M-glucan, D,L-glucan or a saline solution control after being challenged with cold water vibriosis (*Vibrio salmonicida*).

FIG. 6 presents the mortality percentages for each group. The control group had approximately a 96% final mortality percentage. The D,L-glucan treated group of salmon had approximately a 75% final mortality percentage. The M-glucan treated group of salmon had a final mortality of approximately 30%. As can be seen from FIG. 6, glucans elicit an enhanced resistance of Atlantic salmon to disease compared to untreated salmon. Additionally it is also clear that M-glucan Is eliciting a significantly enhanced resistance to disease compared to D,L-glucan.

EXAMPLE VIII

This example demonstrates the effectiveness of M-glucan as an adjuvant with a vaccine to enhance the resistance of fish of the class Osteichthyes, specifically Atlantic salmon (*Salmo salar*) to furunculosis (*Aeromonas salmonicida* subspecies salmonicida).

Pre-smolt Atlantic salmon with an average weight of 30 gram per fish were obtained from a local smolt producer and kept in a 200 liter flow-through tank supplied with aerated fresh water (maintained at approximately 9°–10° C.). A first group of 50 salmon was injected intraperitoneally with a 0.2 ml suspension containing 0.5 mg of M-glucan in an isotonic saline solution. A second group of 50 salmon was injected intraperitoneally with a furunculosis vaccine obtained commercially from Apothekernes Laboratorium A. S. located in Tromso, Norway. A third group of 50 salmon was injected intraperitoneally with a 0.2 ml suspension containing 0.5 mg of M-glucan and the furunculosis vaccine. A control group of 50 salmon was injected intraperitoneally with a 0.2 ml isotinic saline solution. Three months after the injection, all four groups were challenged with furunculosis by introducing a group of salmon injected with furunculosis equaling 10% of the total number of salmon present. The fish were fed with a commercial dry pellet throughout the experiment. All the groups of salmon were kept in the same tank after exposure to furunculosis infected cohabiting fish.

Figure 7:
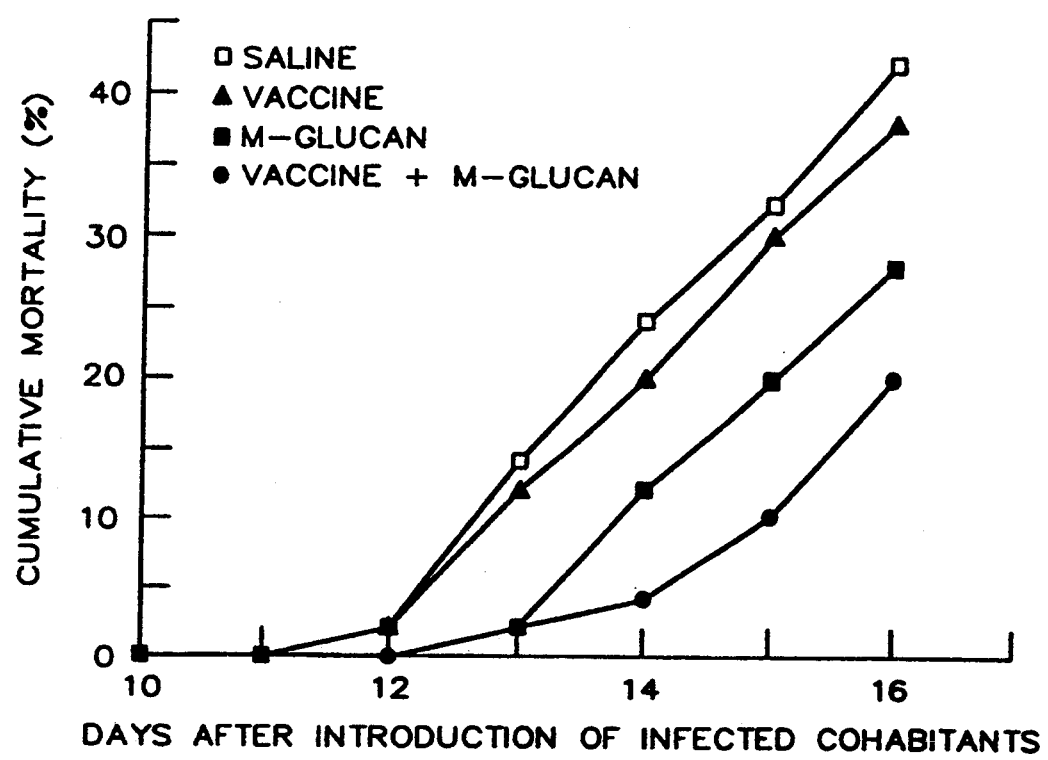
FIG. 7 provides the cumulative mortality in Atlantic salmon treated with M-glucan, a vaccine for furunculosis, M-glucan and a vaccine for furunculosis or a saline solution control after being challenged with furunculosis (*Aeromonas salmonicida* subspecies salmonicida).

FIG. 7 presents the mortality percentages for the test period. The fish treated with the saline solution had a final mortality percentage of approximately 42%. The fish treated with the vaccine had a final mortality percentage of approximately 38%. The fish treated with M-glucan had a final mortality percentage of 28%. The fish treated with a combination of M-glucan and vaccine had a final mortality of 20%. As can be seen from the data the combination of M-glucan with the furunculosis vaccine is the most effective means of enhancing salmon's resistance to furunculosis. These results demonstrates that M-glucan can be effectively employed as an adjuvant with commerical vaccines to enhance resistance of fish to subsequent infection.

EXAMPLE IX

This example demonstrates the effectiveness of M-glucan as an adjuvant with a vaccine to enhance the resistance of fish of the class Osteichthyes, specifically Atlantic salmon (*Salmo salar*) to cold water vibriosis *Vibrio salmonicida*.

Pre-smolt Atlantic salmon with an average weight of 30 grams per fish were obtained from a local smolt producer and kept in a 200 liter flow-through tank supplied with aerated fresh water (maintained at approximately 8°–10° C.). One group of 150 fish was fed a commercial dry pellet enriched with glucan (1 g/kg diet) for four weeks. Two other groups of 150 salmon each were fed the commercial dry pellet without glucan. After four weeks of feeding, the glucan fed group and one of the groups fed without glucan were dip vaccinated by a vaccine against cold water vibriosis (*Vibrio salmonicida*). The vaccine was provided commerically from the company Norbio A/S in Bergen, Norway. The third group of fish was left unvaccinated. After another six weeks, all three groups of fish were challenged by intraperitoneal injection of $1 \times 10^6$ *Vibrio salmonicida* bacterial cells. All feeding was conducted to satiation.

The group of 150 fish fed glucans for four weeks prior to vaccination had a final mortality of 10% after challenge. The vaccinated group fed without glucan bad a final mortality of 44%. The non-vaccinated group fed without glucan had a final mortality of 83%. This data shows the effectiveness of glucan as an adjuvant with commercial vaccines in aquatic animals, particularly salmon, also when administered in the feed.

EXAMPLE X

This example demonstrates the effectivenss of M-glucan as an adjuvant with a vaccine to enhance the resistance of fish of the class Osteichthyes, specifically Atlantic salmon (*Salmo salar*) to classical vibriosis *Vibrio anguillarum* serotype 01.

Pre-smolt Atlantic salmon with an average weight of 30 gram per fish were obtained from a local smolt producer and kept in a 200 liter flow-through tank supplied with aerated fresh water (maintained at approximately 12° C.). A first group of 8 salmon was injected intraperitoneally with a 0.2 ml suspension containing 1.0 mg of M-glucan in an isotonic saline solution. A second group of 8 salmon was injected intraperitoneally with a classical vibriosis vaccine (*Vibrio anguillarum* serotype 01) obtained commercially from Norbio A. S. located in Bergen, Norway. A third group of 8 salmon was injected intraperitoneally with a 0.2 ml suspension containing 1.0 mg of M-glucan and the vibriosis vaccine. A control group of 8 salmon was injected intraperitoneally with a 0.2 ml isotonic saline solution. The fish were fed commercial dry pellet throughout the experiment. All the groups of salmon were kept in the same tank. Six weeks after the injection, all fish were killed by a blow in the head and blood withdrawn from the caudal vein. Specific serum antibody levels against *Vibrio anguillarum* serotype 01 was measured by an ELISA-technique.

Figure 8:
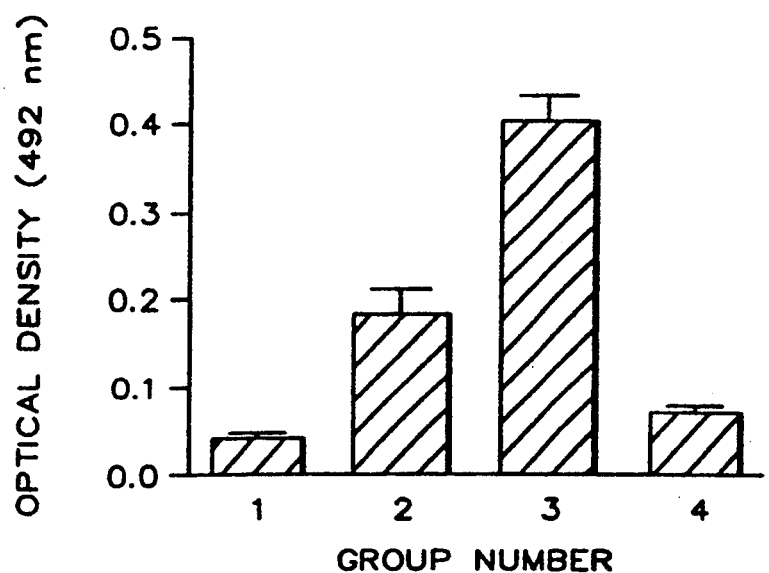
FIG. 8 provides the specific antibody level in Atlantic salmon treated with M-glucan, a vaccine against classical vibriosis (*Vibrio anguillarum* serotype 01), M-glucan and a vaccine against vibriosis or a saline solution control.

FIG. 8 provides the specific antibody level in Atlantic salmon sera treated with M-glucan, the vaccine against classical vibriosis (*Vibrio anguillarum* serotype 01), M-glucan and a vaccine against vibriosis or a saline solution control. The data shows that glucan induces a highly significant (P=0.0015) increase in specific antibody levels against the vaccine.

These results demonstrate that M-glucan can be effectively employed as an adjuvant with commercial vaccines to enhance the resistance of fish to subsequent infection.

EXAMPLE XI

This example demonstrates the effectiveness of M-glucan as an adjuvant with a vaccine to enhance the resistance of fish of the class Osteichthyes, specifically Atlantic salmon (*Salmo salar*) to cold water vibriosis *Vibrio salmonicida*.

Pre-smolt Atlantic salmon with an average weight of 30 grams per fish were obtained from a local smolt producer and kept in a 200 liter flow-through tank supplied with aerated fresh water (maintained at approximately 8°-10° C.). A first group of 8 salmon was injected intraperitoneally with a 0.2 ml suspension containing 1.0 mg of M-glucan in an isotonic saline solution. A second group of 10 salmon was injected intraperitoneally with a cold water vibriosis vaccine (*Vibrio salmonicida*) obtained commercially from Norbio A. S. located in Bergen, Norway. A third group of 8 salmon was injected intraperitoneally with a 0.2 ml suspension containing 1.0 mg of M-glucan and the vibriosis vaccine. A control group of 10 salmon was injected intraperitoneally with a 0.2 ml isotonic saline solution. The fish were fed with a commercial dry pellet throughout the experiment.

All the groups of salmon were kept in the same tank. Ten weeks after the injection, all fish were killed by a blow to the head and blood withdrawn from the caudal vein. Specific serum antibody levels against *Vibrio salmonicida* was measured by an ELISA-technique.

Figure 9:
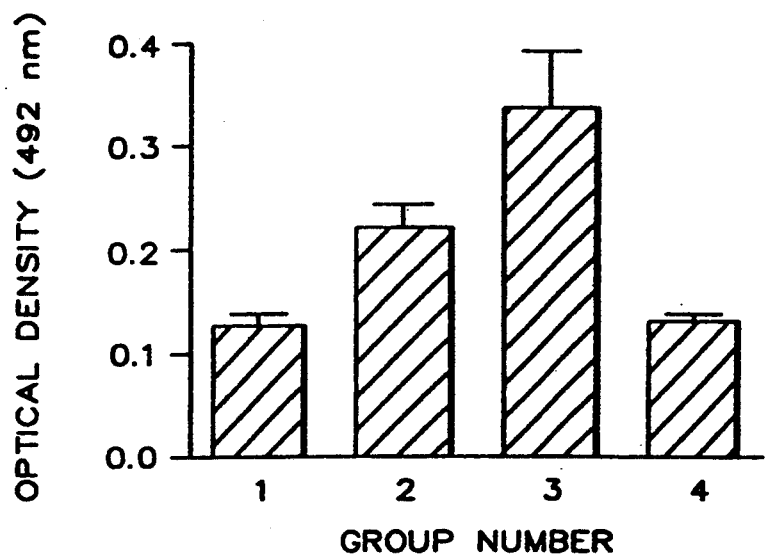
FIG. 9 provides the specific antibody level in Atlantic salmon treated with M-glucan, a vaccine against cold water vibriosis (*Vibrio salmonicida*), M-glucan and a vaccine against cold water vibriosis or a saline solution control.

FIG. 9 provides the specific antibody level In Atlantic salmon sera treated with M-glucan, the vaccine against cold water vibriosis (*Vibrio salmonicida*), M-glucan and a vaccine against cold water vibriosis or a saline solution control. The data shows that glucan induces a significant (P=0.04) increase in specific antibody levels against the vaccine.

These results demonstrate that M-glucan can be effectively empolyed as an adjuvant with commercial vaccines to enhance the resistance of fish to subsequent infection.

EXAMPLE XII

This example demonstrates the relative percentage protection conferred by the M-glucan on fish of the class Osteichthyes, specifically Atlantic salmon. The data in Table 2 was collected using procedures similar to those in Examples II-VIII with the modification noted in Table 2.

As can be seen from Table 2, M-glucan provides significant protection to fish of the class Osteichthyes, specifically salmon, against a variety of diseases.

| Amount of Glucan can per fish | Bacteria | Time from inj. of glucan to challenge | No of Fish per group Control/Glucan | Mean wt of fish | Mortality (%) Control/Glucan | Relative percentage protection (RPP) |
| --- | --- | --- | --- | --- | --- | --- |
| 2.5 mg | *V. salmonicida* ($10^6$) | 4 weeks | 108/80 | 35 | 94/30 | 68 |
| 2 mg | *V. salmonicida* ($10^5$) | 3 weeks | 50/42 | 20 | 74/14 | 81 |
| 2 mg | *V. salmonicida* ($5 \times 10^5$) | 3 weeks | 48/41 | 20 | 96/32 | 67 |
| 2 mg | *V. salmonicida* ($10^5$) | 4 weeks | 50/41 | 20 | 94/37 | 61 |

| Amount of Glucan can per fish | Bacteria | Time from inj. of glucan to challenge | No of Fish per group Control/Glucan | Mean wt of fish | Mortality (%) Control/Glucan | Relative percentage protection (RPP) |
|---|---|---|---|---|---|---|
| 2 mg | V. salmonicida ($5 \times 10^5$) | 4 weeks | 50/34 | 20 | 100/47 | 53 |
| 2 mg | V. salmonicida ($10^5$) | 3 weeks | 40/38 | 20 | 44/18 | 59 |
| 2.5 mg | V. anguillarum ($2.4 \times 10^6$) | 8 weeks | 107/71 | 35 | 32/15 | 53 |
| 2.5 mg | V. anguillarum ($6 \times 10^6$) | 8 weeks | 112/90 | 35 | 56/33 | 41 |
| 2 mg | V. anguillarum ($5 \times 10^4$) | 3 weeks | 40/36 | 20 | 78/33 | 58 |
| 200 μg | V. anguillarum ($5 \times 10^4$) | 1 week | 29/29 | 20 | 76/45 | 41 |
| 200 μg | V. anguillarum ($5 \times 10^4$) | 1 week | 30/30 | 20 | 100/53 | 47 |
| 100 μg | V. anguillarum ($5 \times 10^4$) | 1 week | 30/29 | 25 | 73/41 | 44 |
| 2 mg | Y. ruckeri ($10^4$) | 3 weeks | 45/48 | 20 | 64/44 | 31 |

Legend to Table 2 a) The indicated amounts of M-glucan suspended in 0.2 ml of saline were injected intraperitoneally (i.p.) into each fish. The control fish were injected t.p. with 0.2 ml saline. The fish were challenged 1 to 8 weeks later by i.p. injection of the bacterial pathogan. The dose per fish is shown in parentheses. In each experiment the total mortality in each group was summed up when the mortality had levelled off, that is 40 days after inoculation in experiment 1; 20 days after inoculation in experiment 2, 3, 4, 5, 6 and 12; 25 days after inoculation in experiment 7 and 8; nd 13 days after inoculation in experiment 9, 10, 11 and 12. The relative percentage protection (RPP) is defined by the following formula:

$$RPP = 100\% \left(1 - \frac{\% \text{ mortality in the glucan group}}{\% \text{ mortality in the control group}}\right)$$

b) In experiment 7 and 8 the fish were challenged 4 weeks after Injection of glucan with, respectively, $8 \times 10^3$ and $7 \times 10^4$ Vibrio anguillarum serotype 01. As no mortality occured the fish were rechallenged 8 weeks after injection of glucan.

EXAMPLE XIII

This example demonstrates the effectiveness of M-glucan as a prophylactic medicament in enhancing shellfish of the subphylum Crustacea specifically Giant tiger shrimp's (Penaeus monodon) resistance to disease.

Juvenile Giant tiger shrimp (Penaeus monodon) were stocked to a density of 200 PL50 in each of 6 fiberglass tanks supplied with sterilized sea water on a flow-through system. The shrimp were continuously fed by automatic feeder during daylight hours, either commercial shrimp feed (3 tanks) or commercial feed enriched with 5 grams of glucan from Saccharomyces cerevisiae per kg of feed. The shrimp were fed for 5 weeks before they were subjected to a challenge by adding into each tank a homogenate in sea water of moribund shrimp from a commercial shrimp farm. Such shrimp were carriers of virus and a mixed flora of secondary infectants (e.g. Vibrio harengii and Vibrio parahemolytiens). The number of shrimp in each tank were recorded after 7 weeks. The data showed a total mortality of 80% during 7 weeks in the control group and 50% in the group fed the glucan enriched diet.

This data demonstrates the the effectiveness of orally administered glucan as a prophylactic medicament in enhancing the survival of shrimp in aquaculture.

That which is claimed is:

1. A process for the production of a yeast glucan from Saccharomyces cerevisiae comprising:
   (a) alkali-extracting Saccharomyces cerevisiae with an aqueous alkali solution to provide a first insoluble yeast residue;
   (b) alkali-extracting said first insoluble yeast residue with an aqueous solution of NaOH wherein the alkali extraction is performed about 2 to about 5 times to provide a second insoluble yeast residue and recovering the insoluble yeast residue after each alkali extraction;
   (c) washing said second insoluble yeast residue with water at a pH in the range of about pH4 to about pH7 thereby providing a third insoluble yeast residue and recovering the insoluble yeast residue after each wash;
   (d) hydrolyzing said third insoluble yeast residue with acetic acid wherein the hydrolysis is performed about 3 to about 10 times to provide a fourth insoluble yeast residue and recovering the insoluble yeast residue after each hydrolysis; thereafter
   (e) boiling said fourth insoluble yeast residue in water wherein the boiling of said fourth insoluble yeast residue is performed about 2 to about 6 times to provide a fifth insoluble yeast residue and recovering the insoluble yeast residue after each boiling; and
   (f) boiling said fifth insoluble yeast residue in ethanol wherein the boiling in ethanol of said boiled fifth yeast residue is performed about 2 to about 6 times to provide a sixth insoluble yeast residue and recovering the insoluble yeast residue after each boiling; thereafter
   (g) washing said sixth yeast residue with water wherein the washing of said sixth yeast residue is performed about 2 to about 6 times to provide a yeast glucan and recovering the insoluble yeast glucan after each wash.

2. The product of the process of claim 1.

* * * * *